(12) United States Patent
Norton et al.

(10) Patent No.: US 10,912,583 B2
(45) Date of Patent: Feb. 9, 2021

(54) ACCESS DEVICE WITH ANCHORING BODY AND MODULAR INSERTS AND SUPPORT STRUCTURE FOR SUPPORTING ACCESSORIES USED IN MINIMALLY INVASIVE SURGICAL PROCEDURES

(71) Applicant: Axcess Instruments Inc., Tyler, TX (US)

(72) Inventors: Michael J. Norton, Tyler, TX (US); Noel D. Ischy, Tyler, TX (US)

(73) Assignee: Axcess Instruments Inc., Tyler, TX (US)

( * ) Notice: Subject to any disclaimer, the term of this patent is extended or adjusted under 35 U.S.C. 154(b) by 0 days.

(21) Appl. No.: 16/376,165

(22) Filed: Apr. 5, 2019

(65) Prior Publication Data

US 2019/0231390 A1   Aug. 1, 2019

Related U.S. Application Data

(63) Continuation of application No. 15/098,301, filed on Apr. 13, 2016, now Pat. No. 10,278,730.

(60) Provisional application No. 62/277,427, filed on Jan. 11, 2016, provisional application No. 62/238,245, (Continued)

(51) Int. Cl.
| | |
|---|---|
| *A61B 17/02* | (2006.01) |
| *A61B 17/34* | (2006.01) |
| *A61M 13/00* | (2006.01) |
| *A61M 39/02* | (2006.01) |
| *A61B 90/30* | (2016.01) |
| *A61B 17/00* | (2006.01) |

(52) U.S. Cl.
CPC ...... *A61B 17/3423* (2013.01); *A61B 17/3421* (2013.01); *A61B 90/30* (2016.02); *A61M 13/003* (2013.01); *A61M 39/02* (2013.01); *A61M 39/0247* (2013.01); *A61B 2017/00283* (2013.01); *A61B 2017/00477* (2013.01); *A61B 2017/3445* (2013.01); *A61B 2017/3466* (2013.01); *A61B 2017/3482* (2013.01); *A61B 2017/3484* (2013.01); *A61M 2039/0261* (2013.01); *A61M 2039/0279* (2013.01); *A61M 2210/1021* (2013.01)

(58) Field of Classification Search
CPC .................................................. A61B 17/3423
See application file for complete search history.

(56) References Cited

U.S. PATENT DOCUMENTS

| | | |
|---|---|---|
| 6,551,270 B1 | 4/2003 | Bimbo et al. |
| 6,811,546 B1 | 11/2004 | Callas et al. |

(Continued)

FOREIGN PATENT DOCUMENTS

WO   WO-2014192788 A1   12/2014

OTHER PUBLICATIONS

Supplementary European Search Report for European Patent Application No. EP16824846.6, dated Feb. 1, 2019.

*Primary Examiner* — Jan Christopher L Merene
(74) *Attorney, Agent, or Firm* — Locke Lord LLP; Scott D. Wofsy (57) ABSTRACT

An access port is disclosed for use in minimally invasive surgical procedures performed within a patient's abdominal cavity, which includes a body defining a bore configured to guide at least one surgical instrument into the abdominal cavity, and concave and convex anchoring regions for securing the access port relative to the abdominal cavity.

6 Claims, 9 Drawing Sheets

Related U.S. Application Data filed on Oct. 7, 2015, provisional application No. 62/192,872, filed on Jul. 15, 2015.

(56) References Cited

U.S. PATENT DOCUMENTS

| | | |
|---|---|---|
| 7,751,870 B2 * | 7/2010 | Whitman ............... A61B 1/313 |
| | | 600/476 |
| 8,795,289 B2 | 8/2014 | Fowler et al. |
| 9,017,251 B2 | 4/2015 | Stopek |
| 2006/0247500 A1 | 11/2006 | Voegele et al. |
| 2009/0012477 A1 | 1/2009 | Norton et al. |
| 2009/0030276 A1 * | 1/2009 | Saadat ............... A61B 1/00089 |
| | | 600/112 |
| 2009/0036745 A1 | 2/2009 | Bonadio et al. |
| 2010/0204548 A1 | 8/2010 | Bonadio et al. |
| 2010/0217087 A1 | 8/2010 | Bonadio et al. |
| 2010/0240958 A1 | 9/2010 | Abrams et al. |
| 2010/0324375 A1 | 12/2010 | Piskun |
| 2011/0245844 A1 * | 10/2011 | Jinno ..................... A61B 34/71 |
| | | 606/130 |
| 2011/0306832 A1 * | 12/2011 | Bassan ............... A61B 1/00009 |
| | | 600/109 |
| 2013/0137932 A1 | 5/2013 | Piech |
| 2013/0274559 A1 | 10/2013 | Fowler et al. |
| 2013/0289354 A1 * | 10/2013 | Ainsworth ............ A61B 17/02 |
| | | 600/204 |
| 2014/0094655 A1 | 4/2014 | Newman |
| 2015/0094533 A1 * | 4/2015 | Kleiner ............. A61B 1/00154 |
| | | 600/109 |
| 2015/0141755 A1 * | 5/2015 | Tesar .................. G02B 21/368 |
| | | 600/111 |
| 2015/0297299 A1 * | 10/2015 | Yeung ............... A61B 17/3421 |
| | | 600/102 |
| 2016/0022146 A1 | 1/2016 | Piron et al. |
| 2016/0174814 A1 * | 6/2016 | Igov ................... A61B 1/0051 |
| | | 600/106 |
| 2016/0302826 A1 | 10/2016 | Prati |

\* cited by examiner

ACCESS DEVICE WITH ANCHORING BODY AND MODULAR INSERTS AND SUPPORT STRUCTURE FOR SUPPORTING ACCESSORIES USED IN MINIMALLY INVASIVE SURGICAL PROCEDURES

CROSS-REFERENCE TO RELATED APPLICATIONS

This application is a continuation of U.S. patent application Ser. No. 15/098,301, filed Apr. 13, 2016, which claims the benefit of and priority to U.S. Provisional Patent Application Ser. No. 62/192,872, filed Jul. 15, 2015, U.S. Provisional Patent Application Ser. No. 62/238,245, filed Oct. 7, 2015, and U.S. Provisional Patent Application Ser. No. 62/277,427, filed Jan. 11, 2016, the disclosures of which are hereby incorporated by reference in their entireties.

BACKGROUND OF THE INVENTION

1. Field of the Invention

The subject invention is directed to surgery, and more particularly, to an anchored access port having an attachment to support accessories, such as imaging and lighting devices, used in minimally invasive surgical procedures performed within the abdominal cavity of a patient, including, but not limited to, laparoscopic surgical procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized gas such as carbon dioxide, to create what is referred to as a pneumoperitoneum. The insufflation can be carried out by a surgical access device (sometimes referred to as a "cannula" or "trocar") equipped to deliver insufflation gas, or by a separate insufflation device, such as an insufflation (veress) needle. Introduction of surgical instruments into the pneumoperitoneum without a substantial loss of insufflation gas is desirable, in order to maintain the pneumoperitoneum.

During laparoscopic procedures, a surgeon makes three to four small incisions, between 12 mm and 25 mm in length depending upon the device type, usually no larger than about twelve millimeters each, which are typically made with the surgical access devices themselves, often using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain a desired pressure within the cavity by sealing between the trocar and the surgical instrument being used, while still allowing at least a minimum freedom of movement of the surgical instruments. Such instruments can include, for example, scissors, linear staplers, grasping instruments, and occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar.

Anchoring means must also be provided for securing the trocar or cannula to a patient's abdominal wall during a procedure to prevent the access device from inadvertently withdrawing from the incision through which it has been extended. This is typically accomplished using sutures that are passed through eyelets or similar tie-down features provided on the housing of the trocar or cannula. However, the sutures that are used in this manner can often cause increased trauma to the patient, add complexity to the surgical procedure and create obstructions near the surgical site making it more difficult for the surgeon to operate.

In many of these surgical procedures, several access ports are required, each one dimensioned to receive a particular surgical instrument for use at the surgical site. One of the access ports is typically configured to receive the endoscopic camera that is used for viewing the abdominal cavity and enabling display of the cavity and the manipulation of the instrumentation and tissue within the body cavity on a video monitor viewed by the surgeon.

Therefore, there is a need in the art for a surgical access device that overcomes many of the disadvantages of prior art surgical access devices, including, among others, those associated with the use of anchoring sutures to secure the access device in place during a surgical procedure. It would also be advantageous to reduce the number of access ports in the abdominal cavity while maintaining the same instrumentation and maneuverability of the instruments within the body cavity. More particularly, it would be advantageous to incorporate certain accessory devices, such as a camera, laser or light source into the access device itself, either integrally or by way of a modular attachment, in order to reduce the number of access ports employed during a surgical procedure.

SUMMARY OF THE INVENTION

The subject invention is directed to a new and useful surgical access port for use in minimally invasive surgical procedures, such as, for example, laparoscopic surgical procedures performed within a patient's abdominal cavity that overcomes the disadvantages associated with prior art surgical access devices, including the use of anchoring sutures to secure the device in place during a procedure.

In an embodiment of the subject invention the surgical access port comprises a body defining an outer periphery and a central axis, and having opposed proximal and distal end portions. The body also has an elongated bore extending therethrough from the proximal end portion thereof to the distal end portion thereof for accommodating the introduction of one or more surgical instruments into the patient's abdominal cavity during a surgical procedure.

The body further includes a convex anchoring region projecting radially outwardly from the distal end portion of the body for securing the access port with respect to an interior surface of the patient's abdominal wall, and a concave anchoring region projecting radially inwardly into the proximal end portion of the body, in a location that is substantially diametrically opposed from the convex anchoring region on the distal end portion of the body, for securing the access port with respect to an exterior surface of the patient's abdominal wall. These anchoring features overcome the need for sutures commonly used to secure an access device in place during a surgical procedure.

In an embodiment of the subject invention, at least one rounded protuberance projects radially outwardly from an outer peripheral wall of the body between the convex anchoring region and the concave anchoring region to further aide in securing the access port with respect to the patient's abdominal wall. Alternatively, a plurality of rounded protuberances project radially outwardly from an outer peripheral wall of the body between the convex anchoring region and the concave anchoring region. In such instances, the rounded protuberances may be distributed circumferentially about the periphery of the body between the convex anchoring region and the concave anchoring region. Furthermore, these rounded protuberances may increase in diameter from the convex anchoring region toward the concave anchoring region in a progressive manner.

In an embodiment of the subject invention, an atraumatic spur projects radially outwardly from the distal end portion of the body, in a location that is diametrically opposed from the convex anchoring region adjacent thereto, to further aide in securing the access port with respect to the patient's abdominal wall.

Preferably, the surgical access port of the subject invention includes an integrally associated or otherwise embedded insufflation conduit for delivering insufflation gas into the patient's abdominal cavity during a laparoscopic procedure. The conduit has a connective fitting associated therewith, such as, for example, a standard luer fitting for enabling connection with a flexible conduit or tube set extending from a source of insufflation gas. Preferably, at least one mechanical seal is seated within the elongated bore of the body to inhibit the egress of insufflation gas from the patient's abdominal cavity.

In an embodiment of the subject invention, an arcuate access slot is also formed in the proximal end portion of the body tapering to a circular exit port formed in the distal end portion of the body, adjacent the elongated bore, for accommodating the introduction of another surgical instrument into the patient's abdominal cavity. The arcuate access slot provides the surgeon with an increased range of mobility when manipulating an instrument during a procedure. Preferably, the arcuate slot includes a mechanical seal to inhibit the egress of insufflation gas therethrough. It is envisioned that additional access slots or bores or differing diameter and/or shape may be provided through the body for accommodating the passage of individual surgical instruments.

As for the primary elongated bore of the access port, it is envisioned that it could be a generally cylindrical bore, and it could extend at an angle relative to the central axis of the body, or it could be coaxially aligned with the central axis of the body. The elongated bore may be laterally offset from the central axis of the body. And, in certain embodiments, the elongated bore would taper from the proximal end portion of the body towards the distal end portion of the body to provide an increased range of instrument mobility. Preferably, the elongated bore has an optimal working diameter in the range of about 12 mm or more to about 5 mm or less, enabling the use of a wide range of surgical instruments with access device 10.

It is envisioned that the body of the access port is generally cylindrical in configuration. It could also be generally frusto-conical in configuration, tapering from the proximal end portion thereof toward the distal end portion thereof. Preferably, the convex anchoring region of the body has an atraumatic leading edge surface that is configured to aide in the percutaneous insertion of the body through an incision in the patient's abdominal wall. Moreover, the convex anchoring region acts as a fulcrum point for the access port body during its insertion through the incision, allowing the surgeon to "shoe-horn" the device into an anchoring position relative to the patient's abdominal wall. The concave anchoring region preferably extends through an arc that runs at least partially about the periphery of the body, and preferably it has atraumatic rounded outer edge surfaces.

In embodiments of the subject invention, the surgical access port further includes a sealed adapter plug configured for intimate engagement within a distal end portion of the elongated bore. The sealed adapter plug can include a single instrument passage having a folded baffle seal seated therein or the like. Alternatively, the sealed adapter plug can include a plurality of instrument pathways, each one for accommodating the passage of an individual surgical instrument through the body of the access port and into the patient's abdominal cavity. The individual instrument pathways provided in the adapter plug can all have a common diameter, or at least one of the instrument pathways provided in the adapter plug can have a different diameter than the others.

For example, at least one of the pathways could have a 10 mm diameter to accept a rigid or flexible laparoscope, another pathway could have a 12 mm diameter to accommodate a linear stapler, such as a GIA device, and yet another pathway could have a diameter of 5 mm to accommodate a grasping instrument or the like. Preferably, a mechanical seal is seated within each of the instrument pathways to inhibit the egress of insufflation gas therethrough during a surgical procedure.

The subject invention is also directed to an access port assembly or kit for use in minimally invasive surgical procedures performed within a patient's abdominal cavity, which includes an access port body defining an outer periphery and a central axis, and having opposed proximal and distal end portions, wherein the body further has an elongated bore extending therethrough from the proximal end portion thereof to the distal end portion thereof. The assembly or kit also includes at least one sealed adapter plug configured for intimate engagement within a distal end portion of the elongated bore of the body, wherein the adapter plug has at least one sealed pathway for accommodating the introduction of one or more surgical instruments into the patient's abdominal cavity.

The assembly or kit preferably includes a plurality of sealed adapter plugs, each one having a different arrangement of instrument pathways provided therein, and each one designed for preforming different surgical procedures. It is envisioned that one or more of the access port bodies could be packaged for sale together with one or more of the sealed adapter plugs to form a kit.

It is envisioned that an insufflation conduit would be operatively associated with either the body or the adapter plug for delivering insufflation gas into the patient's abdominal cavity. The conduit would have a connective fitting associated therewith for connecting the access port to a source of insufflation gas.

The subject invention is also directed to an access port for use in minimally invasive surgical procedures performed within a patient's abdominal cavity, which includes a body defining an outer periphery and a central axis, and having opposed proximal and distal end portions, the body further having an elongated bore extending therethrough from the proximal end portion thereof to the distal end portion thereof for accommodating the introduction of one or more surgical instruments into the patient's abdominal cavity. The body includes an anchoring region projecting radially outwardly from the distal end portion of the body for securing the access port with respect to an interior surface of the patient's abdominal wall, wherein the anchoring region of the body is adapted and configured to support one or more accessories used during a surgical procedure adjacent to the elongated bore of the body.

In one embodiment of the invention, the anchoring region is bifurcated to define a channel for accommodating attachment of a support structure adapted to support one or more accessories used during a surgical procedure. In another embodiment of the invention, the support structure is dimensioned and configured to fit over the anchoring region. In such an instance, the anchoring region is preferably formed from a metal strut or the like.

It is envisioned that the accessories associated with the anchoring region and at least one of the surgical instruments may be selected from the group consisting of an optical imaging device, a camera device, a scope, a video device, a light source, a lighting device, a laser device, a measuring device, a laser measuring device, a signal transmitting device, a signal receiving device, a signal processing device, a memory storage device, a wiring device, a servo driven device, a gear device, an irrigation device and/or a suction device. Other devices and tools are also envisioned.

Preferably, the body includes either connective electrical wiring or fiber optic cables for coupling with or otherwise communicating with one or more of the accessories.

The subject invention is further directed to an access port for use in minimally invasive surgical procedures performed within a patient's abdominal cavity, which includes a body having a central axis and defining a bore configured to guide at least one surgical instrument into a patient's abdominal cavity, and an anchoring region extending radially outward from the body relative to the central axis for securing the access port relative to the abdominal cavity. The anchoring region includes a support structure configured for articulating movement within the abdominal cavity relative to the body.

In certain embodiments, a portion of the anchoring region is integrally formed with the body, and the support structure is detachably coupled to the integrally formed portion of the anchoring region and configured to extend radially outward therefrom relative to the central axis. In various embodiments, the support structure includes a pair of radially extending arms, at least one of which is movable relative to the body. The radially extending arms are preferably spring biased toward a spread open position in which the arms define a gap therebetween, and collapsible to a closed position in which the arms are in contact with one another along a radial length thereof.

In certain embodiments, the support structure includes a mounting board coupled to the radially extending arms and spring biased toward a curved configuration. The mounting board can additionally be configured to elastically deform from the curved configuration toward a substantially flat configuration when the pair of radially extending arms are moved from the spread open position to the closed position for insertion into or removal from the abdominal cavity.

The subject invention is also directed to an access port for use in minimally invasive surgical procedures performed within a patient's abdominal cavity, which includes a body defining a bore configured to guide at least one surgical instrument into a patient's abdominal cavity, and an anchoring region including a pair of arms extending radially relative to a central axis of the body, the arms biased toward a spread open position in which the arms define a gap therebetween, and are configured to support at least one accessory used during a surgical procedure.

In certain embodiments, the anchoring region includes a cone-shaped module integrally formed with the body and detachably coupled to the pair of radially extending arms. The anchoring region can include a mounting board substantially arcuately aligned with a radially outer surface of the cone-shaped module when the arms are disposed in the spread open position. In certain embodiments, the anchoring region can include a fixed segment and at least one mobile segment, and the mobile segment(s) may be controllable from outside the abdominal cavity.

The subject invention is additionally directed to a kit for use in minimally invasive surgical procedures performed within a patient's abdominal cavity, which includes an access port having a body defining a bore configured to guide at least one surgical instrument into a patient's abdominal cavity, and a first anchoring portion integrally formed with the body. A second anchoring portion is provided which is configured for detachable coupling with the first anchoring portion and articulating movement within the abdominal cavity relative to the body. The second anchoring portion can include a fixed segment and at least one mobile segment, and the at least one mobile segment can be configured for operative association with a control device outside of the abdominal cavity.

These and other features of the surgical access port of the subject invention and the manner in which both are manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the surgical access port of the subject invention appertains will readily understand how to make and use the subject invention without undue experimentation, preferred embodiments thereof will be described in detail herein below with reference to certain figures, wherein.

DETAILED DESCRIPTION OF PREFERRED EMBODIMENTS

Figure 1:
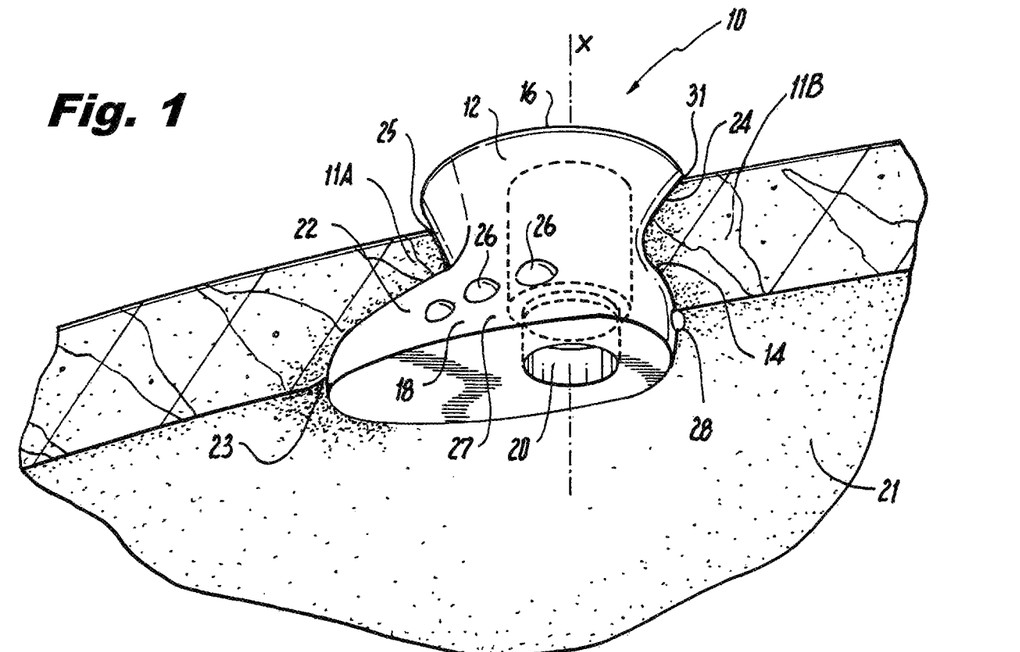
FIG. 1 is a perspective view of the anchored surgical access port of the subject invention installed in an abdominal wall of a patient, which includes an elongated bore, and illustrates a distal convex anchoring region, a proximal concave anchoring region, and a plurality of protuberances of gradually increasing diameter and a distal atraumatic spur.

Referring now to the drawings wherein like reference numerals identify similar structural features or aspects of the subject invention, there is illustrated in FIG. 1 a new and useful surgical access port for use in minimally invasive surgical procedures, such as, for example, laparoscopic surgical procedures performed within a patient's abdominal cavity which is designated generally by reference numeral 10.

Surgical access port 10 provides certain improvements over the advantageous surgical access port devices disclosed in commonly assigned U.S. Pat. No. 9,011,319 to Norton et al., U.S. Patent Application Publication No. 2007/0208312 to Norton et al., U.S. Patent Application Publication No. 2015/0216562 to Norton et al., and U.S. Provisional Patent Application No. 60/779,136 to Norton, the disclosures of which are hereby incorporated by reference herein in their entireties. Surgical access port 10 also provides certain improvements over advantageous surgical access port devices disclosed in related International Patent Publication No. WO 2009/128811 to Norton et al., U.S. Provisional Patent Application No. 61/124,066 to Norton et al., U.S. Provisional Patent Application No. 60/965,404 to Norton et al., and U.S. Provisional Patent Application No. 60/961,802 to Norton et al., the disclosures of which are hereby incorporated by reference herein in their entireties. These improvements relate at least in part to the way in which the access port is anchored with respect the abdominal wall 11 of a patient and to the increased modularity of the access port, adapting it for use in a variety of different surgical procedures, as will be discussed in more detail herein below.

Referring now to FIG. 1, the surgical access port 10 of the subject invention comprises a body 12 defining an outer periphery 14 and a central axis "X", and having opposed proximal and distal end portions 16 and 18. The body 12 also has a single elongated bore or port 20 extending therethrough from the proximal end portion 16 thereof to the distal end portion 18 thereof for accommodating the introduction of one or more surgical instruments into the patient's abdominal cavity 21. The elongated single bore 20 has a working diameter in the range of about between 5 mm or less to about 12 mm or more.

The body 12 further includes a convex anchoring region 22 projecting radially outwardly from the distal end portion 18 of the body 12 for securing the access port 10 with respect to an interior surface 23 of the patient's abdominal wall 11. The body 12 also includes a concave anchoring region 24 projecting radially inwardly into the proximal end portion 16 of the body 12, in a location that is substantially diametrically opposed from the convex anchoring region 22 on the distal end portion 18 of the body 12, for securing the access port 10 with respect to an exterior surface 25 of the patient's abdominal wall 11.

With continuing reference to FIG. 1, in an embodiment of the subject invention, one or more rounded protuberances 26 project radially outwardly from an outer peripheral wall 27 of the body 12 between the convex anchoring region 22 and the concave anchoring region 24 to further aide in securing the access port 10 with respect to the patient's abdominal wall 11. The rounded protuberances 26 may be distributed circumferentially about the periphery of the body 12 between the convex anchoring region 22 and the concave anchoring region 24. Furthermore, these rounded protuberances 26 may increase in diameter from the convex anchoring region 22 toward the concave anchoring region 24, as shown in FIG. 1. It is envisioned that the number, size, shape and location of the protuberances can vary depending upon the application.

In an embodiment of the subject invention, an atraumatic spur 28 projects radially outwardly from the distal end portion 18 of the body 12, in a location that is diametrically opposed from the convex anchoring region 22 adjacent thereto, to further aide in securing surgical access port 10 with respect to the patient's abdominal wall.

Figure 2:
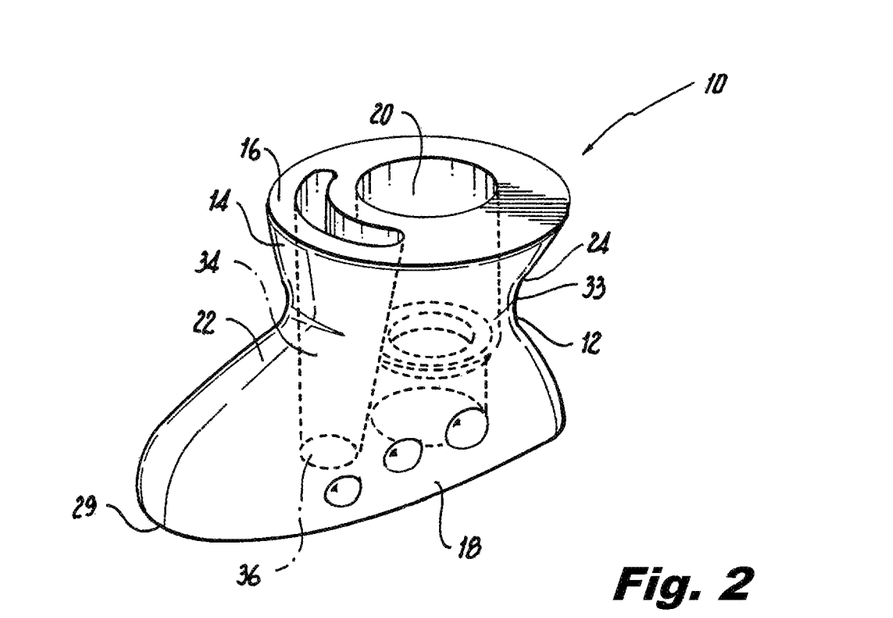
FIG. 2 is a perspective view of the anchored access port of FIG. 1, additionally provided with an arcuate access slot that tapers to a circular exit port.

Referring now to FIG. 2, in an embodiment of the subject invention, an arcuate access slot 34 may be formed in the proximal end portion 16 of the body 12 tapering to a circular exit port 36 formed in the distal end portion 18 of the body 12, adjacent the elongated bore 20, for accommodating the introduction of another surgical instrument into the patient's abdominal cavity 21. The arcuate access slot 34 provides an increased range of motion to the surgeon during a procedure as described in U.S. Patent Application Publication No. 2007/0208312 to Norton et al, incorporated herein by reference in its entirety above. Preferably, the arcuate access slot 34 includes an internal mechanical seal (not shown), which would preferably be located near the exit port 36. It is envisioned that additional access slots or bores of differing diameter and/or shape may be provided through the body 12 of the access port 10 for accommodating the passage of individual surgical instruments of different sizes.

As for the primary elongated bore 20 of the access port 10, it is envisioned that it could be a generally cylindrical bore as shown, and it could extend at an angle relative to the central axis "X" (FIG. 1) of the body 12, or it could be coaxially aligned with the central axis "X" of the body 12. The elongated bore 20 of access port 10 may be laterally offset from the central axis "X" of the body 12. In certain embodiments, the elongated bore 20 can taper from the proximal end portion 16 of the body 12 towards the distal end portion 18 of the body 12.

It is envisioned that the body 12 of the access port 10 is generally cylindrical in configuration. It could also be generally frusto-conical in configuration, tapering from the proximal end portion 16 thereof toward the distal end portion 18 thereof. Preferably, the convex anchoring region 22 has an atraumatic leading edge surface 29 that is configured to aide in the percutaneous insertion of the body 12 through an incision 31 (FIG. 1) in the patient's abdominal wall 11. Insertion and removal of the access port into the abdominal cavity is further discussed below with respect to the embodiment of FIGS. 11-13. Those skilled in the art will readily appreciate that the length, width and height of the convex anchoring region 22 can vary depending upon the application. For example, the convex anchoring region 22 at the distal end portion 18 may be symmetrical around the entire body 12 of the access port 10, or may be elongated on one side of the body 12 in the shape of a boot-tip as shown at the left side of FIGS. 1 and 2. The concave anchoring region 24 preferably extends through an arc that runs at least partially about the periphery 14 of the body 12, and preferably has atraumatic rounded outer edge surfaces 33. It should also be appreciated that the depth, arcuate length and height of the concave anchoring region 24 can vary depending upon the application. It is envisioned that in various embodiments of the subject invention, opposed portions of the abdominal wall 11A, 11B on opposite sides of the incision 31 are received by the concave anchoring region 24 on opposite sides of the body 12, and that the convex region 22 at the distal portion 18 of the body 12 may extend partially or fully under the interior surface 23 of the abdominal wall 11.

Figure 3:
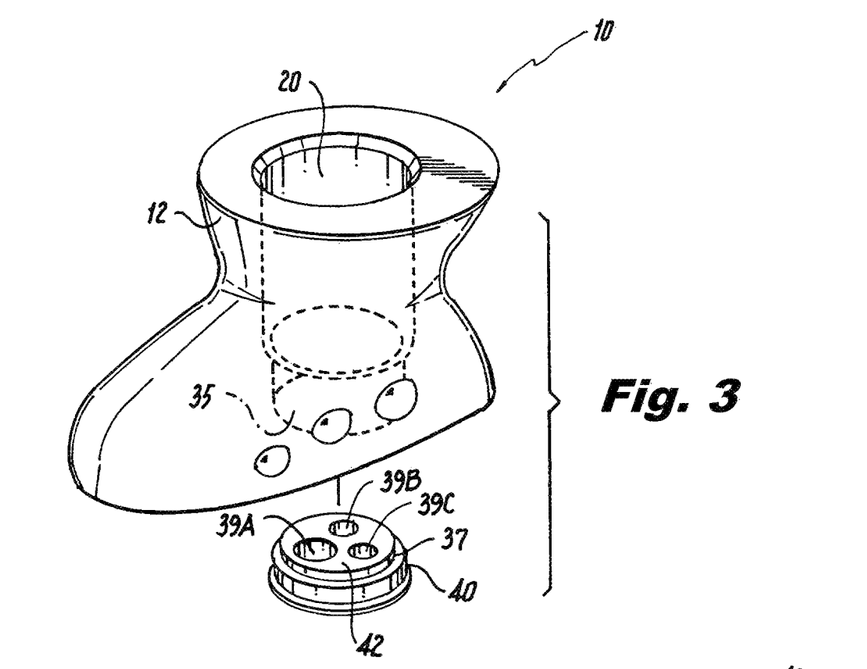
FIG. 3 is an exploded perspective view of an adapter plug configured for intimate engagement within the elongated bore of the surgical access ports shown in FIGS. 1 and 2, which includes a mechanical baffle seal.

Referring to FIG. 3, in embodiments of the subject invention, the access port 10 further includes a sealed adapter plug 40 configured for intimate engagement within a distal end portion 35 of the elongated bore 20. The sealed adapter plug 40 can include a single instrument passage 37 having a folded baffle seal 42 seated therein. Alternatively, the sealed adapter plug 40 can include an insert or integrally formed portion which defines plurality of instrument pathways 39A, 39B, 39C, each for accommodating the passage of an individual surgical instrument (e.g., a camera, scope, light, operating instrument, or other accessory as described herein) through the body 12 of the access port 10, and for guiding respective instruments into the patient's abdominal cavity 21 at select locations.

The individual instrument pathways provided in the adapter plug 40 can all have a common diameter, or at least one of the instrument pathways provided in the adapter plug 40 can have a different diameter than the others. Preferably, a mechanical seal is seated within each of the instrument pathways to inhibit the egress of insufflation gas therethrough. FIG. 3 is an exploded perspective view of an adapter plug 40 configured for intimate engagement within the elongated bore 20 of the surgical access ports shown in FIGS. 1 and 2, which can include mechanical baffle seals.

It is envisioned that certain sections of the peripheral wall 14 of the body 12 of access port 10 in the region of the elongated bore 20, for example, could be formed at least in part by a flexible or otherwise elastomeric material to provide the surgeon with increased range of motion during a surgical procedure.

Figure 4:
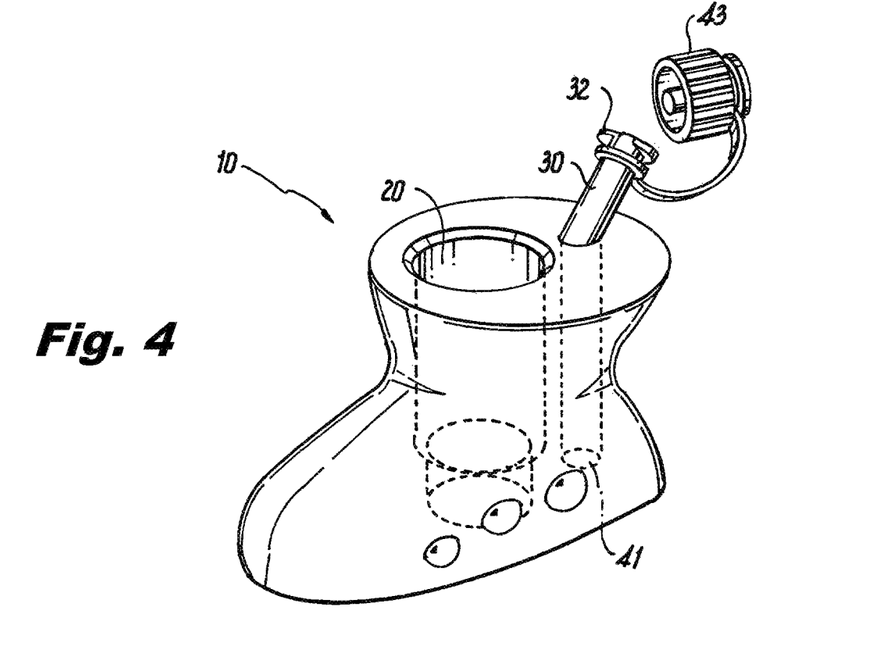
FIG. 4 is a perspective view of the anchored access port of FIG. 1, additionally provided with an insufflation conduit and flexible side walls.

Referring to FIG. 4, the access port 10 can include an embedded insufflation conduit 30 for delivering insufflation gas through the body 12 of the access port 10 into the patient's abdominal cavity 21 at a distal port 41. The conduit 30 has a connective fitting 32 associated therewith, such as, for example, a standard luer fitting for enabling connection with a flexible conduit or tube set extending from a source of insufflation gas. Preferably, at least one mechanical seal (not shown) is seated within the elongated bore 20 of the body to inhibit the egress of insufflation gas from the patient's abdominal cavity 21. The mechanical seal can be in the form of a multi-leaved hemostasis valve, a duckbill valve or as similar mechanical valve used in the surgical arts.

It will also be appreciated that the subject invention is also directed to an access port assembly or kit for use in minimally invasive surgical procedures performed within a patient's abdominal cavity 11, which includes embodiments of the access ports described herein and embodiments of at least one sealed adapter plug 40 described herein. Each sealed adapter plug can have a different arrangement of instrument pathways provided therein, and each different instrument pathway can be designed for performing a different surgical procedure. It is envisioned that one or more of the access port bodies described herein could be packaged for sale together with one or more of the sealed adapter plugs 40 to form a kit.

It is envisioned that the insufflation conduit 30 would be operatively associated with the either the body 12 or the adapter plug 40 for delivering insufflation gas into the patient's abdominal cavity 21. The conduit 30 can include a connective fitting associated therewith for connecting the access port 10 to a source of insufflation gas, and can include a cap 43 for covering or sealing the conduit 30 at a proximal end of the conduit 30 when not in use.

It is envisioned that the access port 10 of the subject invention can be utilized in thoracic surgical procedures and more generally in minimally invasive surgical procedures performed in the properitnoeal spaces lying between the parietal peritoneum and the ventral musculature of the body cavity. In such procedures, it is typically unnecessary to insufflate the body cavity, and therefore, the access port 10 may not include an insufflation conduit or connection as required in laparoscopic procedures performed within the abdominal cavity of a patient.

Figures 5A, 5B:
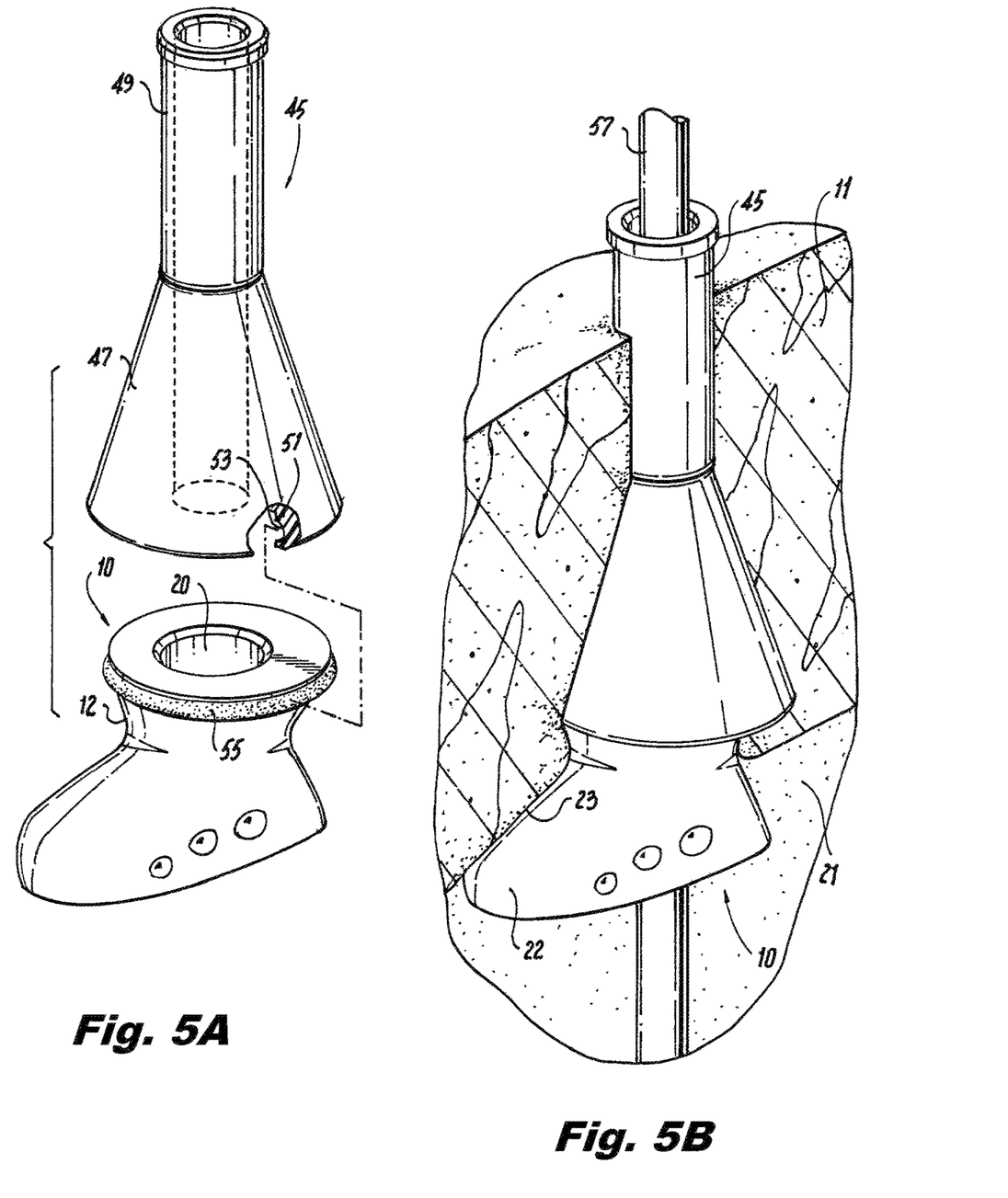
FIG. 5A is an exploded perspective view of the access port of the subject invention provided with a detachable single channel port adapter and extension.
FIG. 5B is a perspective view of the access port and single channel port adapter and extension of FIG. 5A assembled and installed in the abdominal wall of a patient.

Referring to FIG. 5A, the access port 10 may be used in conjunction with a detachable single channel port extension adapter 45 in patients with significant fatty abdominal tissue and/or a thick abdominal wall. The extension adaptor 45 provides a proximal channel extension to the bore 20 with distal conduit 47 and proximal conduit 49 as shown. Distal conduit 47 has an interior surface 51 defining a groove 53 around the circumference thereof for receiving (e.g., by press, interference, or snap fit) an O-ring 55 fixedly attached to the body 12 of access port 10 to fixedly engage the extension adaptor 45 to the body 12 of the access port. Other suitable mechanical engagements and/or fasteners may be utilized. Proximal conduit 49 may be translatable within distal conduit 47 to adjust the overall height of the extension adaptor 45 appropriate to a particular patient, and locked in a particular vertical position by spring loaded pin and slot configurations (not shown) and/or rotatable engagement of threads between the proximal and distal conduits 47, 49. Alternatively, the extension adapter 45 may be provided with a fixed overall height without height adjustment capability.

Referring to FIG. 5B, the access port 10 and extension adapter are shown assembled together and installed through a relatively thick abdominal wall 11 and/or fatty tissue above the abdominal wall 11 with a surgical instrument 57 extending therethrough and into the abdominal cavity 21. As shown, due to the increased overall height, the extension adapter 45 also facilitates location of the distal convex region 22, and particularly the boot-shaped elongated portion of distal convex region 22, under the interior surface 23 of the abdominal wall 11 despite the increased distance between the exterior surface (point of entry into the patient) and the abdominal cavity 21. It will be appreciated that alternative embodiments of the extension adapter 45 may also be utilized, such as, for example, extension adapters which directly couple to the insufflation conduit 30 of FIG. 4 (with a tight seal thereto) rather than to bore 20 for supporting insufflation through a particularly thick abdominal wall or fatty tissue.

Figure 5C:
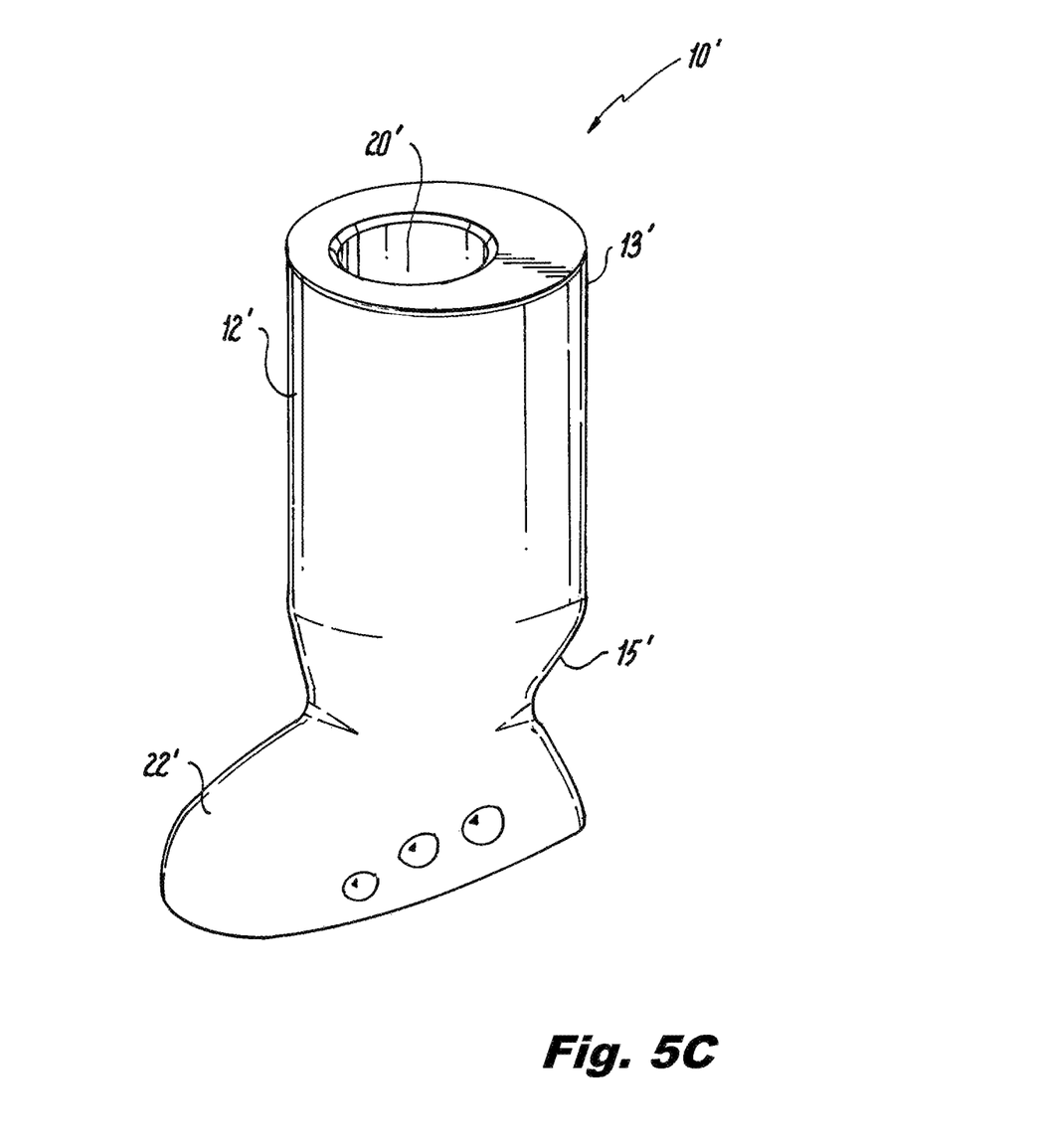
FIG. 5C is a perspective view of another embodiment of the access port of the subject invention, which includes an elongated proximal portion of the body.

Referring to FIG. 5C, another embodiment of the access port 10' is shown in which the body 12' includes an integrally formed elongated proximal portion 13' extending from the proximal concave region 15', and a bore 20' extending all the way through the body 12'. It will be appreciated that different heights may be utilized for the elongated proximal portion 13' of the body 12'. It will also be appreciated that, similar to the detachable single channel port extension adapter 45 described above with respect to FIGS. 5A, 5B, greater heights of proximal portion 13' (and thus greater elongation of the entire body 12') will facilitate use of the access port 10' in patients with a relatively thick abdominal wall and/or fatty tissue above the abdominal wall, and placement of distal convex region 22' underneath the abdominal wall. The access port 10' can also be formed such that the body 12' is elongated with the entire length thereof defining a large proximal concave region and a distal convex region in order to provide increased surface area in the concave region for receiving the abdominal wall and/or fatty tissue above the abdominal wall to better anchor the access port 10'. Other shapes can be utilized.

Figure 6:
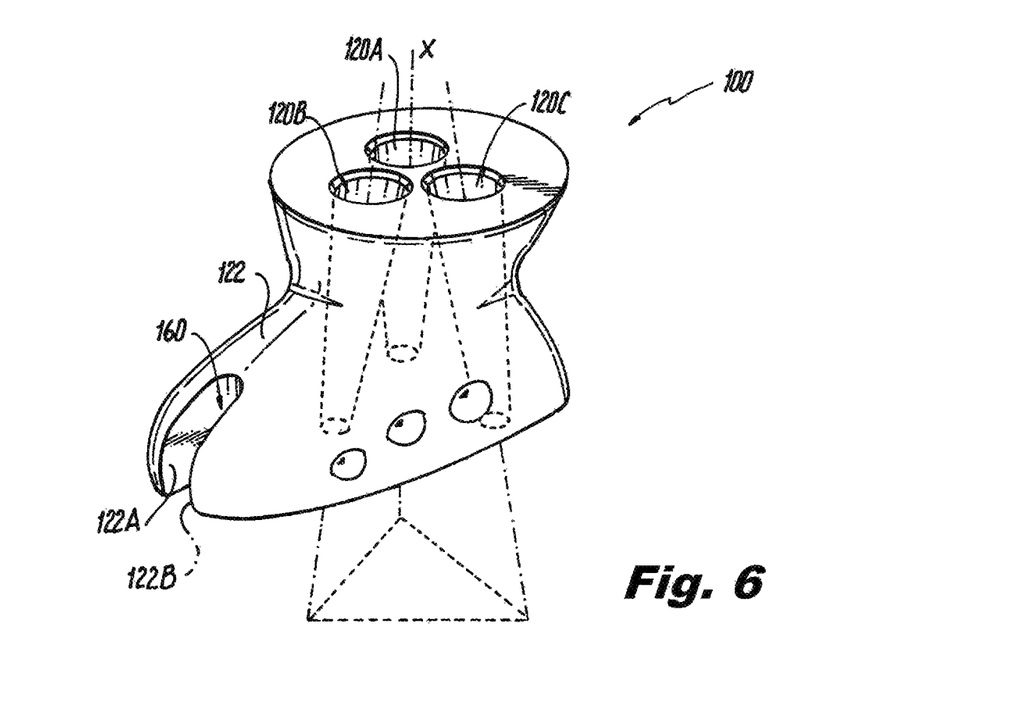
FIG. 6 is a perspective view of another embodiment of the access port of the subject invention, which includes three diverging ports and an anchoring portion which is bifurcated and includes flat exterior surfaces defining a channel to accommodate a support structure for accessories used in minimally invasive surgical procedure.

Referring to FIG. 6, another embodiment of the access port 100 of the subject invention is shown which is similar to access port 10, but includes three diverging ports 120A, 120B, 120C, and a distal anchoring region 122 which is bifurcated, with flat exterior surfaces 122A, 122B defining a channel 160 configured to accommodate a support structure for accessories used in minimally invasive surgical procedure. The diverging ports 120A, 120B, 120C are configured to direct separate surgical instruments to exit the access port 100 in a tri-pod formation (e.g., at one hundred and twenty degree angles apart from one another). The ports 120A, 120B, 120C may also be conical in shape with larger proximal apertures and smaller distal apertures as shown to allow the surgeon to pass a given surgical instrument at slightly different angles through the exit apertures. Other angles relative to axis X may be used for the ports 120A, 120B, 120C.

Figure 6A:
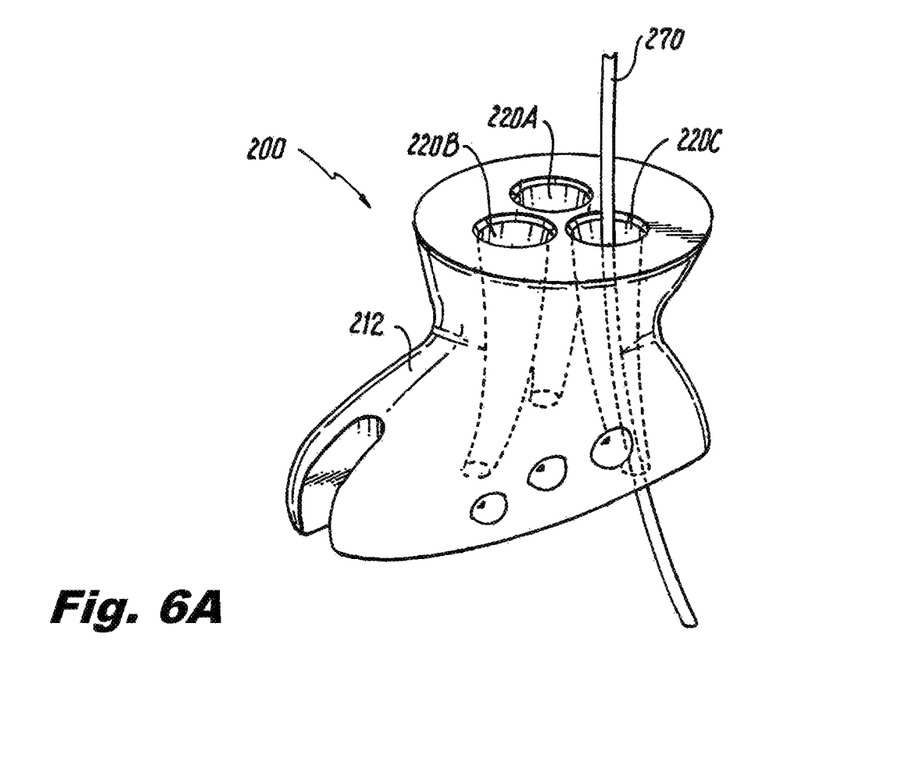
FIG. 6A is a perspective view of another embodiment of the access port of the subject invention, which includes three diverging curved ports and a flexible instrument with shape memory extending through one of the diverging curved ports.

Referring to FIG. 6A, another embodiment of the access port 200 of the subject invention is shown which is similar to access port 100, but includes three diverging ports/channels 220A, 220B, 220C extending through the body 212 which are curved. As shown, a flexible yet resilient surgical instrument 270 with shape memory extends through one of the diverging curved ports 220C, passes through the bend of the port 220C, and exits port 220C straight. It will be appreciated that in this configuration, the exit angle of the surgical instruments passing through the diverging ports will be fixed assuming that the surgical instruments are thick enough that the walls defining the bends in the ports force the surgical instruments to bend. It is envisioned that an elastic resilient spring material be utilized for the surgical instrument 270 such that it has shape memory and is biased toward a straight configuration, yet sufficiently flexible to navigate the bend of the curved ports. It will also be appreciated that in certain embodiments, the ports defined by the access port 200 can converge, intersect, or crisscross within the body of the access port 200 without physically intersecting one another prior to diverging from the access port 200. Crisscrossing or converging ports can, in certain embodiments, facilitate a reduction in the overall size of the access port 200 by making better use of the interior space thereof. The above described structure in conjunction with a plurality of channels through a single access port facilitates advancing surgical instruments into the abdominal cavity through a single access location (where the access port enters the incision), and outward in the abdominal cavity relative to this single access location in a straight controlled manner.

Figure 7:
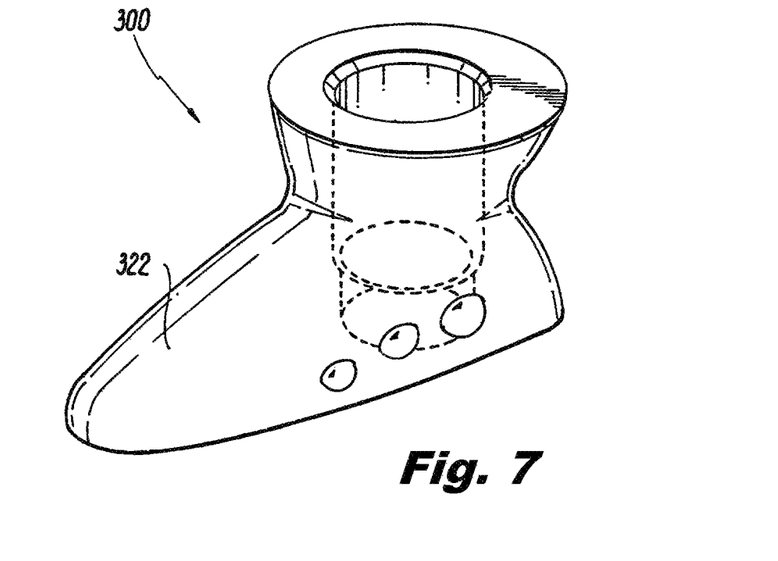
FIG. 7 is a perspective view of yet another embodiment of the access port of the subject invention, which includes an elongated integrally formed distal convex anchoring region.

Referring to FIG. 7, another embodiment of the access port 300 of the subject invention is shown which is similar to access port 10, but with extra elongation of the boot tip shaped distal anchoring region 322.

It will be appreciated that in the various embodiments of the access ports of FIGS. 1-7, the various distal boot tipped shape convex anchoring regions described are integrally formed with the respective access port bodies. As this convex region may be placed under the abdominal wall, it provides additional surface area for interfacing to and anchoring the access port to the abdominal wall, and additional surface area on an opposite side of the distal anchoring region for supporting surgical accessories, including, for example, an optical imaging device, a camera device, a video device, a light source, a lighting device, a laser device, a measuring device, a laser measuring device, a signal transmitting device, a signal receiving device, a signal processing device, a memory storage device, a wring device, a servo driven device, a gear device, an irrigation device and/or a suction device.

For example, the distal anchoring region may define an internal chamber for housing these devices, and/or may fix them to the external surface thereof. Other devices and tools are also envisioned. In certain embodiments, the body of the access device may include either connective electrical wiring or fiber optic cables for coupling with or otherwise communicating with one or more of the accessories.

Figure 8:
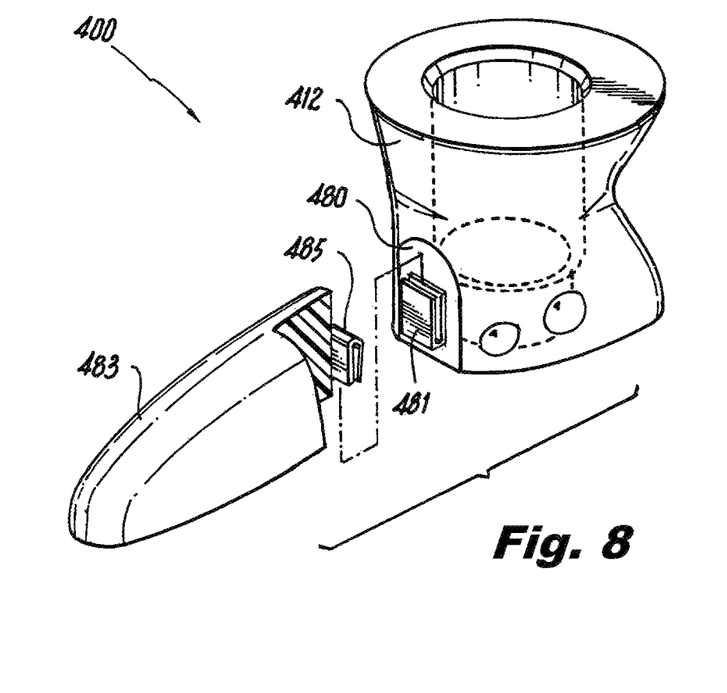
FIG. 8 is an exploded partial cutaway perspective view of yet another embodiment of the access port of the subject invention, which includes a truncated anchoring region with a strut for receiving an anchoring sleeve having an integral flange and configured as a support structure for accessories used in minimally invasive surgical procedures.

Referring to FIG. 8, an alternative embodiment of the access port 400 is provided in which the body 412 includes a truncated anchoring region 480 with a strut 481 configured to detachably couple to a modular anchoring sleeve 483 via an integral flange 485. The modular anchoring sleeve 483 may be configured as a support structure for accessories (e.g., situated inside and/or on the bottom of the sleeve 483) used in minimally invasive surgical procedures. One end of the anchoring sleeve 483 is shown partially cut away in FIG. 8 in order to illustrate the integral flange 485 and its connection to the strut 481. Additional or alternative suitable mechanical attachment mechanisms and/or fasteners may be utilized.

It will be appreciated that anchoring sleeve 483 functions as a modular boot tip device similar to the integrally formed distal anchoring region of the embodiments of the access port described above, but which is attachable to and detachable from the body 412 of the access device 400. The modular anchoring sleeve 483 may be configured to carry wiring, fiber optic cable, and/or lens washing tubing, and can define an interior space to accommodate a multiplicity of devices, machines, measuring devices, computer processors/memory, lighting, imaging, camera, video, laser, laser measuring devices for distance and lighting quality, servos, gears and mounting equipment, support wiring, and transmitters. The modular anchoring sleeve 483 can be alternatively or additionally be provided with an attachment surface for the camera and/or lighting to perform surgical visualization, and can be provided with space and an attachment surface for support equipment, and/or a clear lens at its inferior surface and/or all surfaces. The anchoring sleeve 483 can include a Bluetooth connection to monitor a viewing device, first person view/vison known as FPV with transmission to a viewing monitor or GPS device worn on the head or FPV goggles, and a waterproof lens and housing.

The anchoring sleeve 483 can define internal space configured to accommodate one or more side exiting LED strips (e.g., one or more flat or curved LED strips), a single or multiple adjustable LED lights, a wire harness, wiring tape, as well as the camera and lighting. The camera can be extendible and/or a lighting housing can be attached to the base of the anchoring sleeve 483. The camera or light can be mounted to rotate relative to the anchoring sleeve 483, or can have a flexible mount.

The anchoring sleeve 483 can be provided with a passageway to allow a flexible imaging device, a longitudinal instrument slot to position an endoscope, camera or lighting, and an elastomeric sleeve to provide a seal for an instrument slot and a separate seal for an imaging device control housing.

An attachable lighting source can be mounted to a flexible endoscope or camera scope to provide optimal lighting conditions for surgical procedures requiring more advanced multidirectional lighting to optimally function with the endoscopic camera. This would allow a larger endoscope or unlighted scope with camera (more advanced optics with zoom and increased number of pixels) only to pass through the sealed channel in the anchoring sleeve 483.

It will be appreciated that these surgical accessories may be used in conjunction with any of the embodiments of the access port discussed herein, such as, for example, inside or underneath the integrally formed convex boot tip shaped anchoring regions of FIGS. 1-7.

Figure 9:
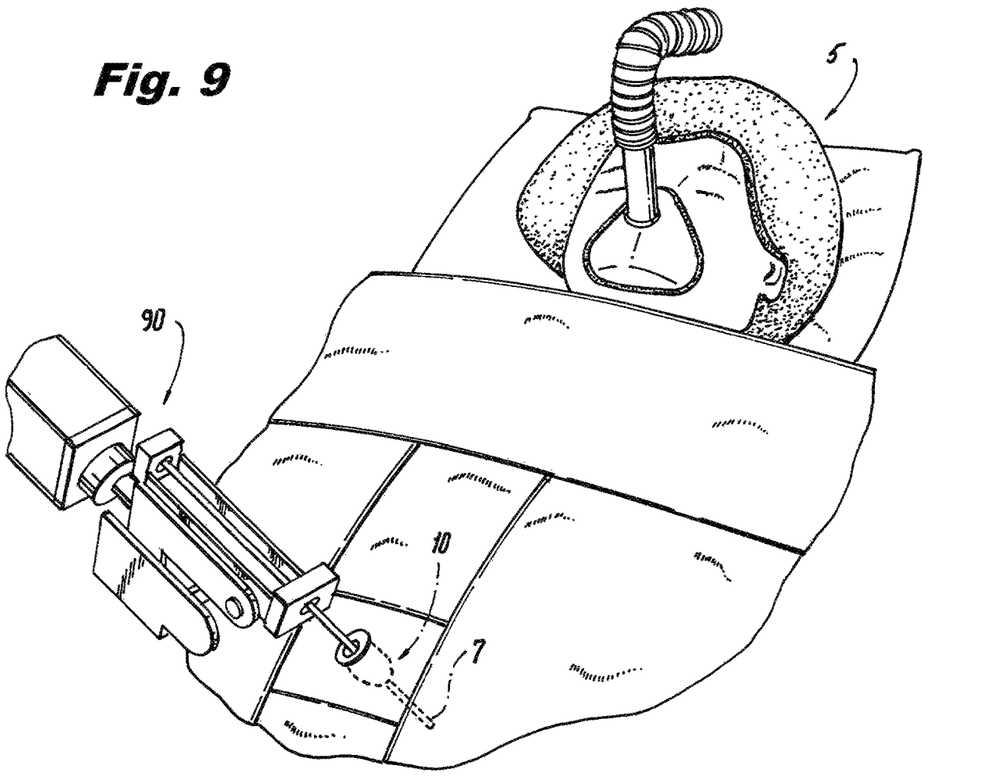
FIG. 9 is a schematic illustration of an example function of the access port of the subject invention, including a depiction of the access port in use with a robotic arm that can operate multiple surgical instruments under vision through a camera associated with the anchoring portion of the access port.

Referring to FIG. 9, the access device 10 is schematically illustrated in use with a robotic arm 90 that can operate one or more surgical instruments 7 under vision through a camera associated with the anchoring portion of the access device 10 installed in a patient 5. It is envisioned that the access device 10 can be provided with one or more passageways for robotic instruments and/or one or more passageways for standard manual instruments such as a clipper, scissors, suction irrigator, grasper, stapler, robotic or manual flexible or rigid endoscope or modular boot tip imaging/lighting device. The access device 10 can be used with an overhead robotic C-arm with six or more degrees of motion controlling one or more instruments. The overhead robotic arm 90 can control or supply support equipment, imaging device/equipment, scope, and a flexible endoscope. The access device 10 can be used with robotic control devices platforms attached to an operating bed such that they can be moved into and out of the operating field area and allow full access to the operating table if the need arises to convert to a standard laparoscopic procedure or open procedure, and the transition wound not be encumbered by machinery.

Figure 10:
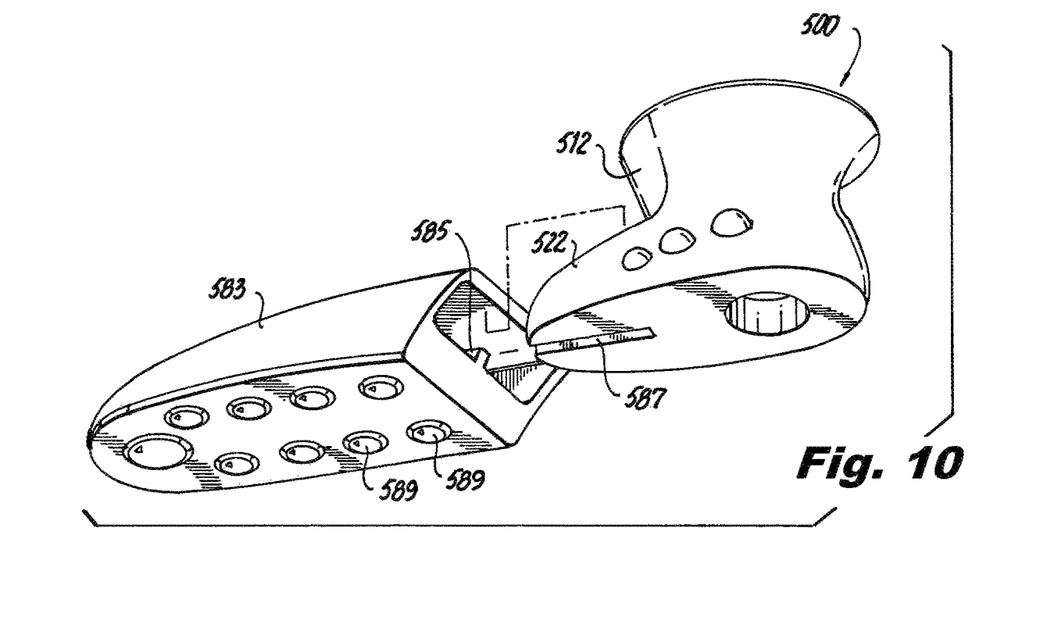
FIG. 10 is a perspective exploded view of another embodiment of the access port of the subject invention, which includes a detachable sleeve supporting surgical accessories which detachably couples to an elongated anchoring region of the access port.

Referring to FIG. 10, an alternative embodiment of the access port 500 is provided in which neither the body 512 nor the distal anchoring boot-tip shaped convex region 522 is truncated, but a modular anchoring sleeve 583 is provided which slides over the convex anchoring region 522, and couples thereto by an elongated pin 585 slot 587 arrangement. The anchoring sleeve 583 may be configured as a support structure, and provided with all the surgical accessories discussed above, which may interface to or communicate with the abdominal cavity through apertures or transparent bottom surfaces 589 at the bottom of the anchoring sleeve 583.

Figures 11, 12:
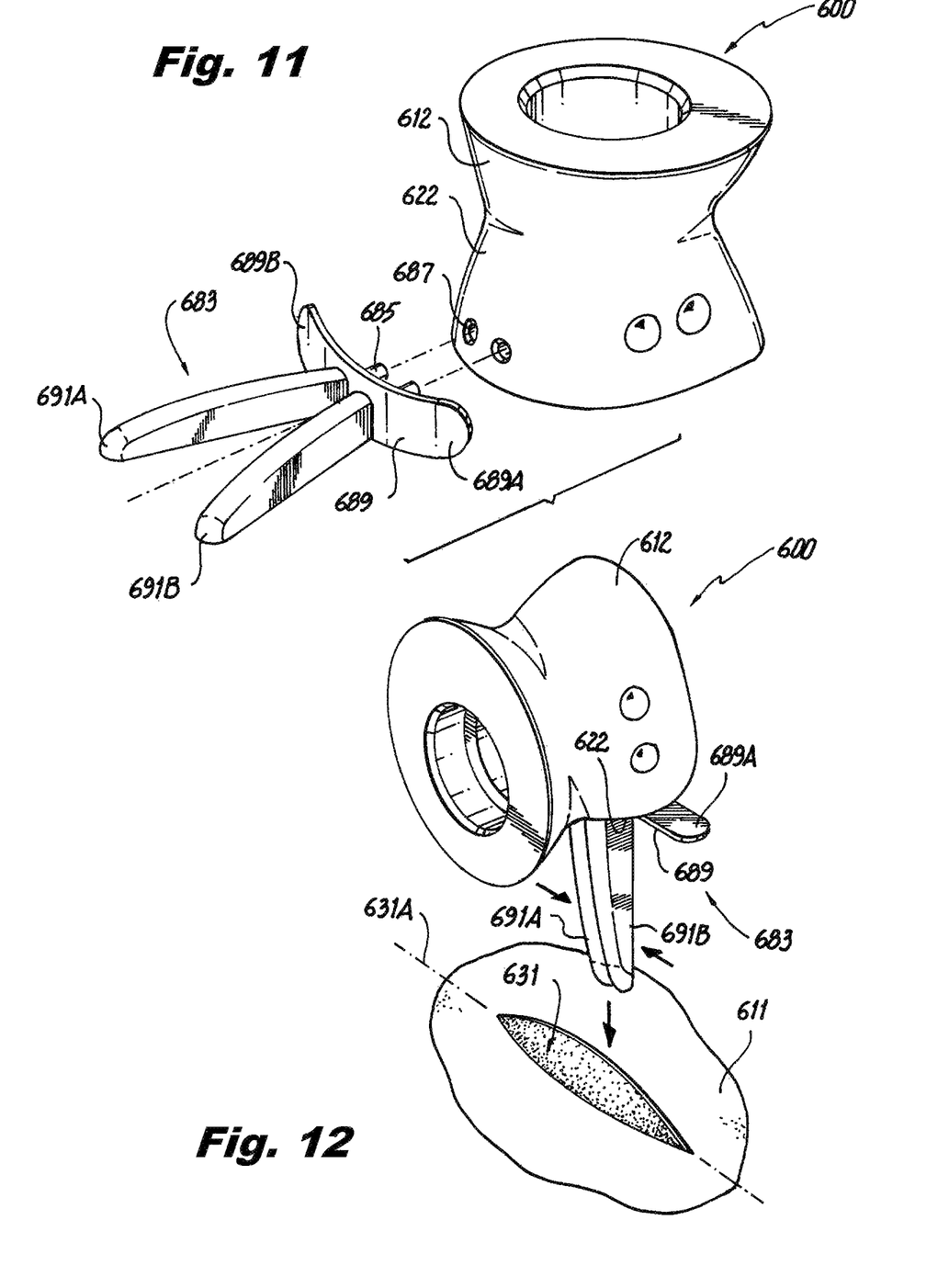
FIG. 11 is an exploded perspective view of yet another embodiment of the access port of the subject invention, which includes an exemplary multi-segment boot tip module in a spread open position which detachably couples to the access port, and allows for binocular vison within a patient's abdominal cavity.
FIG. 12 is a perspective view of the access port and exemplary multi-segment boot tip module of FIG. 11 in an assembled closed position and oriented for insertion into an incision in the abdominal wall.

Referring to FIGS. 11 and 12, an alternative embodiment of the access device 600 and detachable modular boot tip shaped anchoring region 683 is shown. The modular boot tip 683 detachably couples to a distal convex region 622 of the body 612 of the access device 600 by a peg 685 and hole 687 arrangement, and is configured for movement (e.g., articulating movement) within a patient's abdominal cavity relative to the body 612. The pegs 685 can be configured to lock in place within holes 687 by snap, press, or other suitable fastening. The modular boot tip 683 includes a spring biased mounting board 689 coupled to a pair of radially extending arms 691A, 691B which function as an additional anchoring region and support structure for surgical accessories like the boot tip shaped convex regions and anchoring sleeves described above). One or both of the arms 691A, 691B are movable relative to the body 612 or relative to the integrally formed distal convex region 622 of the access device 600. The pair of radially extending arms 691A, 691B are spring biased toward a spread open position in FIG. 11 having a gap defined therebetween, and collapsible to a closed position (FIG. 12) in contact with one another along a radial length thereof.

An I-Beam coupler or other suitable fastener may be utilized to couple the arms 691A, 691B (binocular boot tips) to the convex region 622 of the body 612 of the access device 600 such that the mounting board 689 is arcuately aligned with the radially outer surface of the convex region 622 in the unloaded (open) position of FIG. 11. Other suitable attachment mechanisms can be utilized.

The mounting board 689 is preferably spring biased toward the curved configuration shown in FIG. 11 when relaxed, with the arms 691A, 691B in the open position, but can also be configured as a compound spring with horizontal and vertical spring loading components to support multidirectional deployment of arms 691A, 691B. The mounting board 689 can lie flush with the convex region 622 when mounted thereto, and can comprise two or more arcuately aligned layers.

The arms 691A, 691B may be manually pinched shut from the open position in FIG. 11 to the closed position in FIG. 12 against the spring bias of the mounting board 689 and/or their own spring bias, thus forcing the mounting board 689 to a substantially flat configuration (e.g., by elastic deformation) as shown in FIG. 12. When the manual pinch of the two arms 691A, 691B is released, the spring bias of the mounting board 689 and/or the spring bias of the two arms 691A, 691B move the arms 691A, 691B back to the open position and the mounting board 689 to the curved configuration of FIG. 11.

Figure 13:
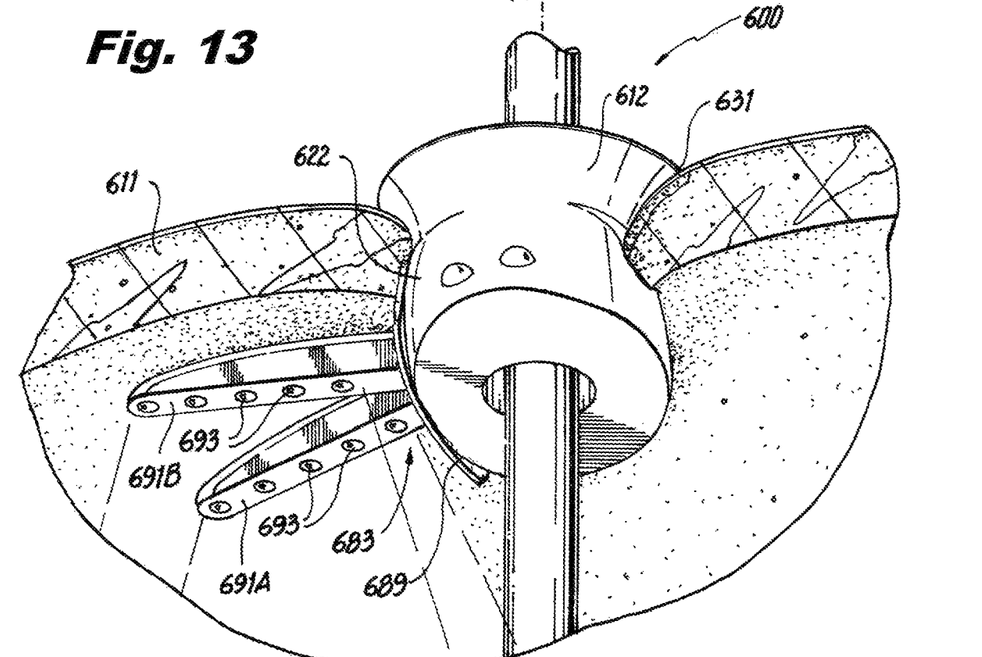
FIG. 13 is a perspective view of the access port and exemplary multi-segment boot tip module of FIGS. 11-12 in a spread open position, and installed in the abdominal cavity of a patient.

Referring to FIG. 13, as illustrated, each arm 691A, 691B of the modular boot tip shaped anchoring device 683 extends radially outward relative to the body 612 of the access device 600 (e.g., relative to a central axis X of the body 612), and is adapted and configured to carry various accessories, such as a light, a camera, wiring, and various other surgical accessories as discussed above, which may interface to or communicate with the abdominal cavity 621 through apertures or transparent bottom surfaces 693 at the bottom of the modular anchoring device 683.

It will be appreciated that once the modular anchoring device 683 is coupled to the convex region 622, the arms 691A, 691B may be manually pinched together to the closed position, and held closed at the base thereof while inserted into the small incision 631 in the abdominal cavity 621. As the mounting board 689 will be in a substantially flat configuration during insertion of the arms 691A, 691B (FIG. 12) with its lateral edges 689A, 689B offset from the radially outer surface of the distal convex region 622, it will substantially align with axis 631A of the incision 631 in the abdominal wall 611, and thus can be inserted perpendicular thereto behind the radially extending arms 691A, 691B. In other words, in the closed position, the arms 691A, 691B and the mounting board 689 together function as an atraumatic leading edge which aids in percutaneous insertion of the entire anchoring region 683, 622 into the abdominal cavity 621.

Once the arms 691A, 691B and mounting board 689 are advanced distally beyond the abdominal wall 611 and into the abdominal cavity 621, the base of the arms 691A, 691B may be released. The spring bias of the arms 691A, 691B and/or mounting board 689 will move the arms 691A, 691B to the spread open (expanded) position with a gap therebetween as shown in FIG. 13. It will be appreciated that such expansion/separation of the arms 691A, 691B within the abdominal cavity 621 allows for an increased footprint therein after passing through a small minimally invasive incision 631. Such increased footprint gives greater anchoring capability to the anchoring region 622, 683 of the access device 600, helps prevent inadvertent withdrawal of the access device 600, and provides greater surface area, angles, and options for holding, angling, and utilizing surgical accessories. It will be appreciated that when the access device 600 is removed, the modular anchoring device 683, disposed distal of the body 612, may once again be pinched at the base of the arms 691A, 691B when it reaches the abdominal incision 631. Such contact may be sensed by the surgeon via haptic perception or observed via instrumentation. A closing collar may be placed around the circumference of the arms 691A, 691B, or two steel eyelets may be placed on proximal upper surfaces of the arms 691A, 691B (e.g., one on either arm) to oppose the arms prior to removal to help ensure approximation of the arms to the surgeon. The arms 691A, 691B may alternatively be approximated by a tool. The arms 691A, 691B are preferably constructed to be sufficiently mobile and with blunted edges to avoid injury to the abdominal wall with sudden removal absent such accouterments, even when the arms 691A, 691B are not aligned with the incision 631 in the abdominal wall 611.

It is anticipated the embodiments described above may be used in other spaces such as in a prostatectomy, and in spaces which need not be expanded with insufflation or mechanical retraction. It is also anticipated that one of the arms of the articulating boot tip shaped anchor portion described above with respect to FIGS. 11-13 can be useful as telescopic retractor to provide more exposure by mechanical means. It will be appreciated that the methodology described above with respect to FIGS. 11-13 may be similarly utilized for the other embodiments of the access device described herein, using the various convex anchoring regions described above (e.g., the convex regions integrally formed to the body of the access device or the modular anchor attachments which detachably couple to the body of the access device) as the atraumatic leading edge to guide insertion of the access device into the incision.

The exemplary modular anchoring device 683 illustrated and described with respect to FIGS. 11-13 above may be used in conjunction with various embodiments of the inventive disclosure described herein. The increased workspace provided by arms 691A, 691B may contain or be equipped with, for example, lighting, a camera, zoom lenses, laser measuring devices, servos, receivers and transmitters, first person vision equipment, GPS capability, computer components and mainboards to support part or all of the equipment. Mechanical channels may be contained within or traverse to the additional workspace provided for purposes of lighting, laparoscopic cameras, flexible endoscopes, insufflation, irrigation, suction, smoke evacuation, operating instruments or lasers, and other energy sources. The modular anchoring device 683 is preferably provided with a water resistant or waterproof interior environment, with suitable seals applied to joints and entrance and exit sights thereof to preserve the desired operating environment.

It is also anticipated that the access device 600 with modular anchoring device 683 may be utilized, for example, in the abdomen, properitoneal space, cranium and Thorax, or in an organ lumen such as the stomach, bladder, bowel, or other spaces. The anchoring device 683 may additionally or alternatively include a fixed segment (e.g., one of arms 691A, 691B) and at least one mobile segment (e.g., the other of arms 691A, 691B) rather than configuring both arms 691A, 691B to be movable relative to the body 612 or integrally formed anchoring region 622 of the access device 600.

Figure 14:
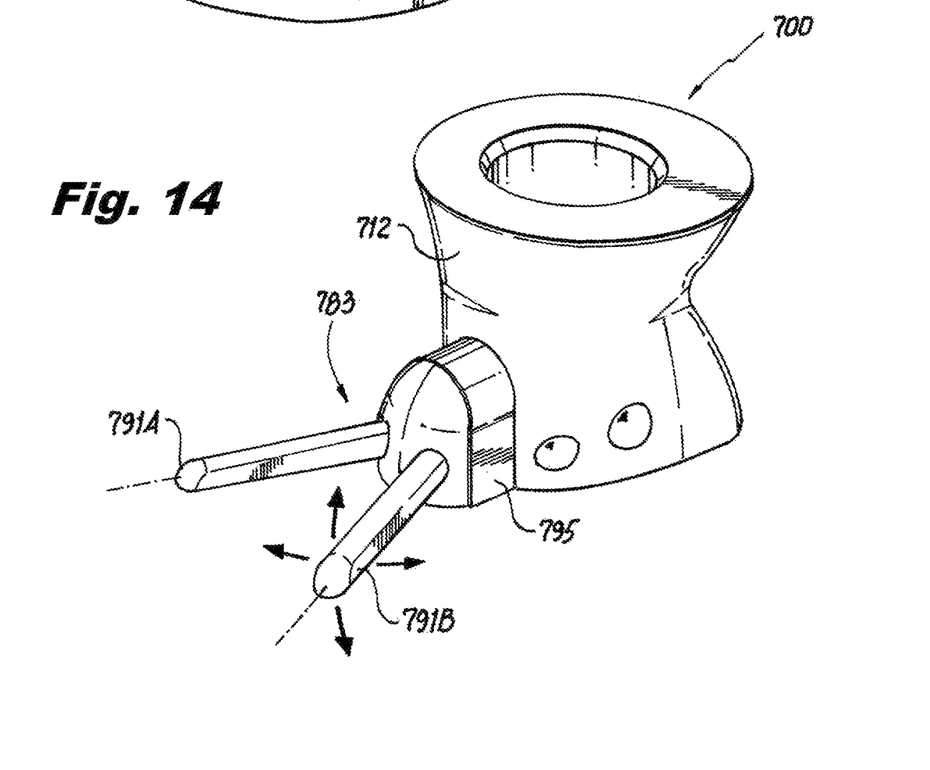
FIG. 14 is a perspective view of another embodiment of the access port and multi-segment boot tip module of the subject invention, and includes a control device which is coupled to the access port body and the multi-segment boot tip module, and is in operative communication with an outside device for control of the arms of the multi-segment boot tip module.

Referring to FIG. 14, an alternate embodiment of an access device 700 in accordance with the subject invention is shown with an alternate multi-segment modular boot tip shaped anchoring device 783. The modular anchoring device 783 includes a control module 795 which detachably couples to the access port body 712 via any suitable mechanism (e.g., such as described with respect to FIG. 11) and a pair of arms 791A, 791B, and is in operative communication with an outside device (e.g. the robot arm 90 described with respect to FIG. 9) for control of bilateral movement of one or both of the arms 791A, 791B. It will be appreciated that such mobile arms 791A, 791B may be controllable from outside the abdominal cavity via manual or automated control devices.

It will be appreciated that alternative embodiments of modular anchoring devices and the attachment mechanisms between the modular anchoring devices and the bodies of the access devices can be utilized, including, for example, ball and socket joints, mortise and tenon, and male and female pin and receiver. Such joints may be configured in sequence or in parallel as may be required to adapt to particular operative environments. In certain embodiments, one of the boot tip shaped anchoring segments/arms/tips may be fixed in position with one or more additional segments which are mobile such that the fixed segment provides primary support and anchoring to the mobile segments. The mobile segments may attach to the fixed segment, or may be directly attached to the body of the access device. The body of the access device may be provided in other shapes, and is not limited to conical or truncated conical shapes, if different shapes are more effective to meet requirements of a particular operation and operative field. The mobile segments (e.g., mobile arms) can be motorized from within. Alternatively, the fixed segments may function as a primary housing for mechanical and controller devices with the mobile segments functioning in, for example, various of the other capacities listed above. The mobile segments may be controlled by direct control, remote control, first person vision, GPS motion, voice or ocular control, measuring devices, or programmed integrated/co-ordinated movements.

Alternatively, the primary anchoring segment may be mobile and configured to provide an adjustable (simple or compound) angle, thus providing dynamic positioning adaptable to changing requirements as the operation progresses. The body of the access device may additionally provide workspace housing, equipment mounting, and one or more conduits for wiring, fiberoptics, batteries, lighting, cameras or monitoring sensors in addition to any other devices needed to support the above described components and systems.

It will be appreciated that the embodiments of the inventive disclosure described herein allow for entry into the abdominal cavity through a single access device in a single incision, modularity both inside the access device body (e.g., with detachable seals and inserts which can fluidly couple and fluidly isolate one or more bores of the access device to/from one or more fluid channels defined by the detachable insert), and outside the access device body (e.g., with detachable anchoring portions and sleeves as described herein). The above described embodiments allow the surgeon to spread outward within the abdominal cavity from one or more ports of the access device, in a variable yet controlled manner while supporting surgical accessories adjacent the body of the access device.

While the subject invention has been shown and described with reference to preferred embodiments, those skilled in the art will readily appreciate that various changes and/or modifications may be made thereto without departing from the spirit and scope of the subject invention as defined by the appended claims.

What is claimed is:

1. A system for performing robotically assisted laparoscopic surgical procedures within a patient's abdominal cavity, comprising:
    a) an access device having an elongated body portion with an elongated bore extending therethrough for accommodating the introduction of surgical instruments into the patient's abdominal cavity and having an anchoring portion that extends radially outwardly from the elongated body portion and includes a curved upper surface and a planar bottom surface defined by a single plane, wherein the elongated bore extends to an opening in the planar bottom surface of the anchoring portion and the curved upper surface of the anchoring portion is configured to shoe-horn the access device through an incision into an anchoring position with respect to an interior wall of the patient's abdominal cavity, a modular anchoring sleeve configured to slide over the anchoring portion and couple thereto, a bottom surface of the anchoring sleeve supports a camera and one or more LED light sources to facilitate surgical visualization of the patient's abdominal cavity as the access device is shoe-horned through the incision into the anchoring position and with the access device installed in the patient's abdominal cavity; and
    b) a robotic arm for operating one or more surgical instruments extending through the elongated bore of the body portion of the access device under vision through the camera associated with the bottom surface of the modular anchoring sleeve.

2. A system as recited in claim 1, wherein the robotic arm is configured as an overhead robotic arm.

3. A system as recited in claim 1, wherein the robotic arm is attached to an operating bed.

4. A system as recited in claim 1, wherein a slot traverses the planar bottom surface and is configured to secure the modular anchoring sleeve.

5. A system as recited in claim 1, wherein the bottom surface of the modular anchoring sleeve includes at least first portion more transparent than a second portion.

6. A system as recited in cam 1, wherein the bottom surface of the modular anchoring sleeve includes a plurality of apertures.

* * * * *